(12) United States Patent
Hayes et al.

(10) Patent No.: US 10,280,396 B2
(45) Date of Patent: May 7, 2019

(54) CULTURED TOBACCO CELLS AS A MATRIX FOR CONSUMABLE PRODUCTS

(71) Applicant: Philip Morris USA Inc., Richmond, VA (US)

(72) Inventors: Alec J. Hayes, Chesterfield, VA (US); Maria Shulleeta, Richmond, VA (US); Jason W. Flora, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 15/838,825

(22) Filed: Dec. 12, 2017

(65) Prior Publication Data

US 2018/0105794 A1 Apr. 19, 2018

Related U.S. Application Data

(62) Division of application No. 13/071,866, filed on Mar. 25, 2011, now Pat. No. 9,862,923.

(60) Provisional application No. 61/318,209, filed on Mar. 26, 2010.

(51) Int. Cl.
  *C12N 5/04* (2006.01)
  *A24B 15/20* (2006.01)

(52) U.S. Cl.
  CPC ............... *C12N 5/04* (2013.01); *A24B 15/20* (2013.01)

(58) Field of Classification Search
  USPC ................................................. 131/352, 353
  See application file for complete search history.

(56) References Cited

U.S. PATENT DOCUMENTS

| | | |
|---|---|---|
| 3,710,805 A | 1/1973 | Tamaki et al. |
| 3,955,317 A | 5/1976 | Gudin |
| 4,459,355 A | 7/1984 | Cello et al. |
| 4,795,855 A | 1/1989 | Fillatti et al. |
| 4,906,577 A | 3/1990 | Armstrong et al. |
| 4,940,838 A | 7/1990 | Schilperoort et al. |
| 4,945,050 A | 7/1990 | Sanford et al. |
| 5,002,890 A | 3/1991 | Morrison |
| 5,015,580 A | 5/1991 | Christou et al. |
| 5,030,573 A | 7/1991 | Petiard et al. |
| 5,168,059 A | 12/1992 | Roberts |
| 5,238,841 A | 8/1993 | Gupta et al. |
| 5,260,205 A | 11/1993 | Nakatani et al. |
| 5,324,707 A | 6/1994 | Yokoyama et al. |
| 5,369,023 A | 11/1994 | Nakatani et al. |
| 5,413,930 A | 5/1995 | Beewar et al. |
| 5,506,136 A | 4/1996 | Beewar et al. |
| 5,668,295 A | 9/1997 | Wahab et al. |
| 5,684,241 A | 11/1997 | Nakatani et al. |
| 5,885,826 A | 3/1999 | Worden et al. |
| 6,001,642 A | 12/1999 | Tsao |
| 6,074,876 A | 6/2000 | De Block |
| 6,098,536 A | 8/2000 | Knight et al. |
| 6,492,174 B1 | 12/2002 | Pullman et al. |
| 6,586,661 B1 | 7/2003 | Conkling et al. |
| 6,589,780 B2 | 7/2003 | Banerjee et al. |
| 6,700,040 B2 | 3/2004 | Roberts et al. |
| 6,830,928 B1 | 12/2004 | Goethals et al. |
| 6,907,887 B2 | 6/2005 | Conkling |
| 6,911,541 B2 | 6/2005 | Conkling et al. |
| 7,129,393 B1 | 10/2006 | Vainstein et al. |
| 2002/0028512 A1 | 3/2002 | Lin et al. |
| 2003/0073579 A1 | 4/2003 | Lin et al. |
| 2003/0221221 A1 | 11/2003 | Murray |
| 2004/0106199 A1 | 6/2004 | Eliseev |
| 2004/0142467 A1 | 7/2004 | Lin et al. |
| 2004/0242417 A1 | 12/2004 | Lin et al. |
| 2005/0244521 A1 | 11/2005 | Strickland et al. |
| 2006/0030487 A1 | 2/2006 | Lin et al. |
| 2006/0123518 A1 | 6/2006 | Olsen et al. |
| 2006/0225750 A1 | 10/2006 | Koga et al. |
| 2007/0151149 A1 | 7/2007 | Karpinski |
| 2007/0240728 A1 | 10/2007 | Hashimoto et al. |
| 2008/0227088 A1 | 9/2008 | Albino et al. |
| 2009/0038033 A1 | 2/2009 | Bloksberg et al. |
| 2015/0013695 A1 | 1/2015 | McNeal et al. |

FOREIGN PATENT DOCUMENTS

| | | |
|---|---|---|
| GB | 2 203 022 A | 10/1988 |
| GB | 2 234 663 | 12/1991 |
| WO | 2009064771 A2 | 5/2009 |

OTHER PUBLICATIONS

Alliance One International, "*Glossary,*" available at http://www.aointl.com/au/glossary.asp (last visited May 28, 2011).

Iraki et al., "*Extracellular Polysaccharides and Proteins of Tobacco Cell Cultures and Changes in Composition Associated with Growth-Limited Adaptation to Water and Saline Stress,*" 91 Plant Physiology, 54-61 (1989).

(Continued)

*Primary Examiner* — Cynthia Szewczyk
(74) *Attorney, Agent, or Firm* — Buchanan Ingersoll & Rooney LLP

(57) ABSTRACT

Various embodiments are directed to consumable products incorporating a matrix of cultured tobacco cells. Any tobacco variety may be utilized for establishing in vitro tobacco cultures, including native tobacco varieties and genetically modified tobacco varieties derived from any tobacco variety. Various embodiments are directed to methods for producing tobacco products incorporating cellular material and/or extracts derived from tobacco cells cultured in vitro.

6 Claims, 2 Drawing Sheets

(56) References Cited

OTHER PUBLICATIONS

Murashige et al. "*A Revised Medium for Rapid Growth and Bio Assays with Tobacco Tissue Cultures,*" 15 Physiologia Plantarum 473-497 (1962).
Iraki et al., "Alteration of the Physical and Chemical Structure of the Primary Cell Wall of Growth-Limited Plant Cells Adapted to Osmotic Stress," Plant Physiol, (1989) 91, 39-47.
Munnik et al., *Osmotic stress activates distinct lipid and MAPK signaling pathways in plants,* 498 FEBS Letters 172-178 (2001).
*Murashige Skoog—Plant Tissue Culture Protocol,* http://www.sigmaaidrich.com/technical-documents/protocols/biology/murashiige-skooQ.himi (printed Nov. 21, 2016).
European Office Action dated Apr. 1, 2018, in corresponding EP Patent Application No. 11 726 950.6-1401.
Tholakalabavi et al., Effect of Mannitol, and Glucose-Induced Osmotic Stress on Growth, Water Relations, and Solute Composition of Cell Suspension Cultures of Polar (*Populus deltoides* Var. *occidentials*) in Relation to Anthocyanin Accumulation, 30P In Vitro Cell., Dev. Biol. 184-170 (Jul. 1994).

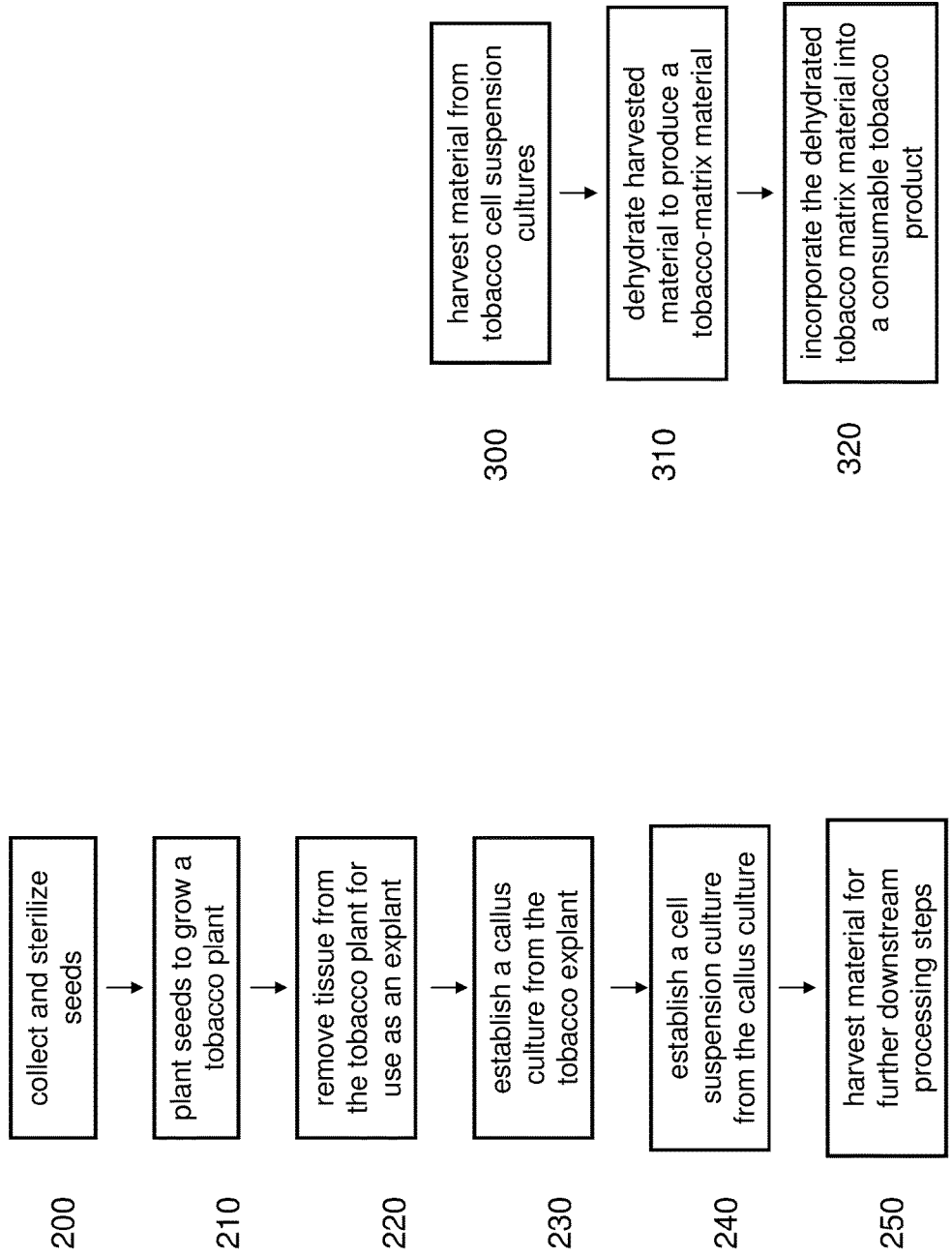

CULTURED TOBACCO CELLS AS A MATRIX FOR CONSUMABLE PRODUCTS

CROSS-REFERENCE TO RELATED APPLICATIONS

This application is a divisional application of U.S. patent application Ser. No. 13/071,866, filed Mar. 25, 2011, which claims priority to U.S. Provisional Patent Application Ser. No. 61/318,209, filed on Mar. 26, 2010, the contents of which is incorporated herein by reference in its entirety for all purposes.

BACKGROUND

Conventionally-grown tobacco tends to be dark in color which is not always desirable. Thus, a need exists for a consumable product lacking dark pigments

SUMMARY

One embodiment of the invention is a method for producing a product, comprising the steps of growing tobacco cells in liquid suspension culture under conditions of osmotic stress and/or saline stress to form a culture material comprising tobacco cells and extracellular matrix; harvesting culture material; drying the culture material to create a tobacco matrix; and incorporating the tobacco matrix into a product.

Another embodiment of the invention is consumable product comprising a matrix of cultured tobacco cells, wherein the matrix of cultured tobacco cells comprises at least 5% by weight extracellular matrix.

BRIEF DESCRIPTION OF THE DRAWINGS

FIG. 2 shows an exemplary method for establishing in vitro cultures of tobacco cells.

FIG. 3 shows an exemplary method for preparing tobacco matrix material from cultured tobacco cells established according to the method illustrated in FIG. 2.

DETAILED DESCRIPTION

Figure 1:
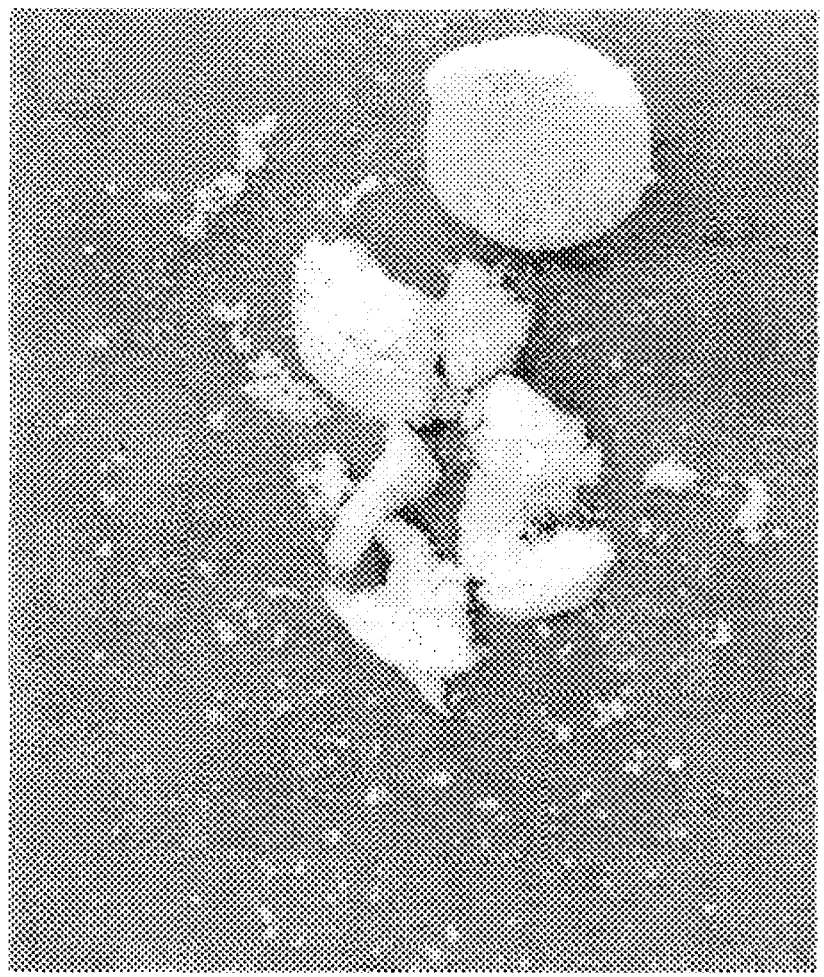
FIG. 1 illustrates an image of exemplary freeze-dried, tobacco cells cultured in vitro that can be incorporated into various smokeless products, as a substitute for conventional tobacco particles, shreds, fine cut or long cut tobacco lamina, and/or as an additive ingredient.

Some factors essential for controlling cellular growth and differentiation have been defined, including various plant growth hormones and differentiation factors that operate alone or in synergistic combinations. For example, by controlling the relative ratio of cytokinin to auxin concentration in a culture medium, in vitro cultures of plant cell suspension exhibiting various properties of interest can be generated. Typically, a callus culture can be established from an initial tissue explant removed from a plant of interest. Culture conditions suitable for initiating and maintaining the proliferative state of callus cultures can be defined experimentally for any plant of interest, such as tobacco plants.

Various embodiments are directed to lit-end (i.e., smokeable) and smokeless products incorporating culture material (including cellular material and/or secreted extracellular material) from tobacco cells cultured in vitro. Any tobacco variety may be utilized for establishing in vitro tobacco cultures, including native tobacco varieties and genetically modified tobacco varieties derived from any tobacco variety, and can be maintained for long periods under proper conditions. Various embodiments are directed to methods for producing smokeless products incorporating culture material from tobacco cells cultured in vitro. Tobacco-based products incorporating various alternative ingredients that can improve the enjoyment of the products, and that can be produced in a cost-effective manner, are highly desirable.

A. Definitions

The term "non-tobacco smoking material" or "tobacco substitute" refers to a material other than tobacco utilized for making smoking articles and smokeless products. For example, the common non-tobacco fillers are organic plant constituents comprising cellulose, including vegetable-based substances, such as rhubarb, plantain, coltsfoot, self-heal, comfrey, stinging nettle, watercress, groundsel, oxtongue, beet, mallow, poppy leaves, sage, walnut, cherry, red beech, hornbeam, maple, hazlenut, goldenregen, prickly broom, eucalyptus, bagasse, lettuce, peanut, soybean, potato, corn, yam, taro, and cocoa, paper, and seaweed.

The term "tobacco extender" or "tobacco supplement" refers to a nontobacco material, natural or synthetic, that can be blended with tobacco in making of smoking articles and smokeless products to produce a desired effect, such as cost savings, alteration of smoke constituents, reduction of tar delivery, improvement of physical characteristics of the products.

The term "tobacco dust" refers to ground tobacco and/or tobacco particles created by tobacco breakage during manufacturing processes.

The term "reconstituted tobacco" refers to tobacco dust, stems, by-products, and equivalents, that may be mixed with a cohesive agent, and that are rolled or cast into a flat sheet of uniform thickness and quality. A sheet of reconstituted tobacco may be cut into any size shreds. Examples of basic sheet processes include dust-impingement process, tobacco-slurry process, impregnation-of-web process, paper process, and extrusion process.

The term "hydroscopic agent" or "plasticizer" refers to humectants and equivalent agents added to tobacco or substituted tobacco to help retain moisture and plasticity, such as glycerin.

The term "without added light" means substantially without exposure to sunlight and with only incidental exposure to artificial light. Preferably, when a plant cell culture is grown without added light, a carbon source (sucrose, for example) is provided in the culture medium.

As used herein, the term "extracellular matrix" denotes material secreted by plant cells. Exemplary components of extracellular matrix include carbohydrates (such as polysaccharides), proteins, and glycoproteins such as proteoglycans. More particularly, exemplary components of extracellular matrix include cellulose, hemicellulose, pectin, and waxes. Additional exemplary components of extracellular matrix are disclosed in U.S. Patent Application Publication No. 2009/0038033, incorporated herein by reference.

As used herein, the term "osmotic stress" refers to culture conditions wherein the osmolarity is sufficiently higher than that needed for the maximum rate of increase in numbers of cells so as to result in a measurable different in one or more cellular traits (such as rate of growth) and/or the extracellular matrix.

As used herein, the term "saline stress" refers to culture conditions wherein the concentration of salt (including but not limited to NaCl) is sufficiently higher than that needed for the maximum rate of increase in numbers of cells so as to result in a measurable different in one or more cellular traits (such as rate of growth) and/or the extracellular matrix.

As used herein, the term "about" when used in conjunction with a stated numerical value or range denotes somewhat more or somewhat less than the stated value or range, to within a range of ±10% of that stated.

B. Methods for Establishing Cultures from Tobacco Explants

FIG. 1 illustrates an image of exemplary freeze-dried, tobacco cells cultured in vitro ("tobacco matrix material") that can be incorporated into a consumable tobacco product, as a substitute for conventional tobacco particles, shreds, fine cut or long cut tobacco lamina, and/or as an additive ingredient. In FIG. 1, the tobacco cells harvested from in vitro cultures were subsequently freeze-dried to produce a light weight, nearly white, and powdery substance that can be utilized for producing various products of interest. Because the cultured tobacco cells are grown in the dark, the cultured tobacco cells appear nearly white, without the formation of dark pigments observed in traditionally grown tobacco leaves. The disclosed tobacco matrix comprises cultured tobacco cells preferably along with extracellular matrix material. The tobacco matrix, which includes tobacco cells as well as extracellular matrix, is preferably substantially without dark pigmentation can be incorporated into various products of interest. A broad range of products, exhibiting a number of attributes of interest, can be produced by varying certain parameters, including selecting suitable tobacco explants utilized to generate tobacco suspension cultures, growing the tobacco suspension cultures under suitable growth conditions, processing the harvested material including tobacco cells by a suitable method, and incorporating the processed tobacco matrix material into various tobacco products.

FIG. 2 shows an exemplary method for establishing in vitro cultures of tobacco cells that can be utilized for the preparation of a tobacco matrix material. A subset of these steps may be sufficient to accomplish the goals described herein. The exemplary method of FIG. 2 comprises: collecting seeds from a tobacco plant of interest and sterilizing their exterior to eliminate unwanted organisms 200; planting seeds to grow a tobacco plant of interest 210; removing tissue from the tobacco plant (for example, from a tobacco stem) for use as an explant 220; establishing a callus culture from the tobacco explant 230; establishing a cell suspension culture from the callus culture 240; and harvesting culture material (which includes tobacco cells and extracellular matrix material) for further downstream processing steps 250.

Accordingly, in harvesting the cells, extracellular matrix associated with and/or secreted by the cells is preferably harvested with the cells to aid in formation of the tobacco matrix material. Preferably the culture material, as measured after drying, includes about 5 to 80% percent secreted extracellular matrix, more preferably about 5 to 50% secreted extracellular matrix, still more preferably about 10 to 25% secreted extracellular matrix. The remainder of the culture material is preferably mostly tobacco cells.

FIG. 3 shows an exemplary method for preparing tobacco matrix material from cultured tobacco cells established according to the method illustrated in FIG. 2. In FIG. 3, harvesting material from suspension cultures 300; dehydrating harvested material to produce a tobacco matrix material 310; and incorporating the dehydrated tobacco matrix material into a consumable tobacco product of interest 320, for example a cigarette or pouched tobacco product.

For illustration, Examples 1-3, provided below, describe the composition of an exemplary growth medium, growth conditions for establishing tobacco callus cultures, growth conditions for generating and subculturing tobacco suspension cultures, conditions for harvesting of tobacco suspension cultures, and conditions for preparing a tobacco matrix material.

Selection of Suitable Culture Media for Growing Tobacco Cells

Under controlled conditions, many types of in vitro cultures derived from an explant derived from a tobacco plant of interest ("tobacco cultures") can be stably established and indefinitely propagated. Tobacco cultures can grow in many types of media, including Murashige and Skoog (MS), which is a commercially available, basic media commonly utilized for supporting the growth of various plant-tissue cultures. Example 1, provided below, describes the preparation of the MS medium and an exemplary method for preparing an explant from the stem of a tobacco plant of interest. A callus culture can be established from the initial explant, which can be propagated by subsequent rounds of subculturing as described in Example 1. Once established, the cultured tobacco cells exhibit characteristics of immortalized cells, and can be propagated indefinitely in a culture medium, in which the cellular growth and division of the cultured cells are limited only by the replenishment of fresh media.

In general, the explant is first introduced into an initiation media in a semi-solid gel form to support the development of solid cell masses ("callus"). A liquid media can be employed at later stages for growing non-aggregated tobacco cell suspensions following the inoculation with the pre-established tobacco callus. In general, the semi-solid gel media can be prepared by combining the components of the liquid media and a gelling agent, such as agar, gellan gum, agarose, and GELRITE®. Methods for the preparation of such media are known to persons skilled in the art, and general formulations are described in U.S. Pat. Nos. 5,236,841; 5,413,930; and 5,506,136, each is which is incorporated herein by reference. As further explained in Example 2, viable tobacco cell suspensions cultures can be established by transferring a callus of tobacco cells into a liquid media, and can be grown in the dark with moderate agitation.

Any steps equivalent to the described steps of the method described herein are also contemplated, including individual steps and combination of steps, known to persons skilled in the art. As one example, in order to add flavors to the tobacco matrix, the culture may be grown in the presence of a flavorant or a flavorant precursor which is taken up by the cells and thence converted to a flavorant. As another example, a callus culture established from a tobacco explant, such as 230, and a cell suspension culture established from a callus culture, such as 240, can be scaled-up in volume and number to accommodate manufacturing levels of biomass (See FIG. 2). Cells can be cultivated in any volume, including small-scale cell cultures having a volume of less than about 20 L. For example, a suitable volume includes an amount less than about 1 L (e.g., 25 ml to 100 ml), from about 1 L to about 5 L, from about 5 L to about 10 L, or from about 10 L to about 20 L. Alternatively, cells can be cultivated in medium-scale cell cultures having a volume from about 20 L and about 500 L, from about 100 L to about 500 L, or from about 20 L to about 2,000 L. Alternatively, cells can be cultivated in large-scale bioreactors having a volume up to about 20,000 L, such as from about 1,000 L to about 10,000 L, from about 2,000 L to about 10,000 L, or from about 1,000 L to about 20,000 L. In general, small-scale devices are limited to a few liters in volume because they rely on surface oxygen transfer to provide aeration for the cells. Examples of small-scale devices include spinner flasks, T-flasks, and roller bottles. Methods for establishing large-scale bioreactors such as stirred tank bioreactors are known by persons skilled in the art (see Armstrong, U.S. Pat. No. 4,906,577 and Morrison, U.S. Pat. No. 5,002,890, each of which is incorporated herein by reference).

Furthermore, the growth/maintenance of cultures and the harvesting of tobacco cells for further downstream processing steps, such as 250, can be automated in part or in its entirety (See FIG. 2). As one method for growing the cell cultures in the dark, the cell suspensions can be grown in light-blocking containers to preclude the activation of photo-sensitive biochemical pathways that may lead to the production of colored pigments. Any light-blocking container can be utilized to reflect, scatter, and/or absorb light, and thus reduce and/or prevent light penetration into the container. Light-blocking containers can be made by incorporating light blocking materials, as one or more coatings or as laminates. A light-blocking material may include any suitable color dye. The light-blocking material can reflect or scatter the light, and/or can absorb the light to prevent exposure of the biological fluid inside the container to the light. The light-blocking material should be capable of blocking ultraviolet (UV) and/or visible light. For example, the light-blocking material can block light wavelengths from about 10 nm to about 1 mm, from about 10 nm to about 400 nm, or from about 400 nm to about 750 nm, or from about 750 nm to about 1 mm. Light-blocking materials suitable for making cell culture containers are known to persons skilled in the art, including polymers, such as various polyesters. For example, polyethylene terephthalate (PET), polyethylene naphthalate (PEN), polyvinyl fluoride (PVF), and tedlar PVF are highly effective in blocking ultraviolet (UV) light. Metals such as stainless steel, for example in a stainless steel bioreactor, are also effective in blocking light.

Culture Conditions to Induce Changes in Cell Surface Extracellular Polysaccharides and/or Polypeptides Preferably, the culture medium is adapted to induce osmotic and saline stress to tobacco cells in suspension cultures in order to cause changes in the composition of the cell surface of cultured cells that promote cellular adhesion and/or the secretion of extracellular matrix. Increasing the amount of extracellular matrix present can aid in the subsequent formation of a cohesive tobacco matrix. For example, the culture medium can be supplemented with an osmotic stress inducer, such as polyethylene glycol ("PEG"), or a saline stress inducer, such as NaCl. For example, the culture medium in which the suspension culture is grown can be supplemented with a sufficient amount of PEG or an equivalent, such as at least 10%, 15%, 20%, 25%, or 30%.

Alternatively, the culture medium can be supplemented with a sufficient amount of NaCl or an equivalent, selected from a range from about 300 mM to about 500 mM. Polyethylene glycol (PEG) can be also referred to as polyethylene oxide (PEO) or polyoxyethylene (POE). The terms "PEG," "PEO," or "POE" may refer polymers of ethylene oxide. These terms can be interchanged, however traditionally, PEG refers to polymers exhibiting a molecular mass below 20,000 g/mol; PEO refers to polymers exhibiting a molecular mass above 20,000 g/mol; and POE refers to a polymer of any molecular mass.

Prior studies have shown that saline-adapted cells and PEG-adapted cells transferred to iso-osmolar mannitol can release significantly more carbohydrates and proteins from their cell walls into the culture medium when compared to unadapted cells (See Iraki et al., "Extracellular Polysaccharides and Proteins of Tobacco Cell Cultures and Changes in Composition Associated with Growth-limiting Adaptation to Water and Saline Stress," Plant Physiology, Vol. 91: p54-61 (1989), incorporated herein by reference). There, tobacco cells (*Nicotiana tabacum* L. cv W38) were maintained in liquid suspension culture, such as MS medium and adapted to grow in a medium supplemented with either 30% PEG (−28 bar) or 428 mM NaCl (−23 bar).

Selection of Suitable Explants from Tissues of Tobacco Plants

To provide a source of culture material (including cellular material and/or secreted extracellular material), an in vitro culture of tobacco cells can be established from an "explant." An explant is an organ, tissue, or cells derived from a plant, and are cultured in vitro for the purpose of starting a plant-tissue culture. Suitable explants to initiate in vitro cultures include any portion of a tobacco plant that demonstrates substantial metabolic activity, responsiveness to growth factors, and accessibility by physical dissection. For establishing cultures for micro-propagation, the tissues most frequently utilized as suitable explants include meristematic ends of plants, such as the stem tip, auxiliary bud tip, and root tip. The meristematic ends can exhibit high rates of cell division, and can either produce or store growth factors necessary for growth and/or differentiation, including auxins and cytokinins. In general, explants derived from aerial portions of a plant located above the soil may be preferable over root explants because potentially contaminating microflora from aerial explants can be less difficult to remove than from root explants that can adhere more tightly to undesirable microflora. Alternatively, uncontaminated explants can be obtained by removing portions from seedlings that are grown from surface-sterilized seeds. The hard surface of a seed is less permeable to penetration by more stringent sterilizing agents than more delicate vegetative tissue.

Selection of Suitable Tobacco Varieties

In some embodiments, suitable tobacco explants can be derived from any native tobacco variety selected from the genus *Nicotiana*, various species of *Nicotiana*, including *N. rustica* and *N. tabacum* (e.g., LA B21, LN KY171, TI 1406, Basma, Galpao, Perique, Beinhart 1000-1, and Petico). Other species include *N. acaulis, N. acuminata, N. acuminata* var. *multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N.×sanderae*.

In some embodiments, suitable tobacco explants can be derived from non-native tobacco plants, including genetically-modified tobacco plants (e.g., transgenic plants) derived from any tobacco variety, including the varieties provided above.

Suitable plants for transformation include any plant tissue capable of transformation by various methods of transforming plants known by persons skilled in the art, including electroporation, micro-projectile bombardment, and *Agrobacterium*-mediated transfer as described, for example, in U.S. Pat. No. 4,459,355 that discloses a method for transforming susceptible plants, including dicots, with an *Agrobacterium* strain containing a Ti plasmid; U.S. Pat. No. 4,795,855 that discloses transformation of woody plants with an *Agrobacterium* vector; U.S. Pat. No. 4,940,838 that discloses a binary *Agrobacterium* vector; U.S. Pat. No. 4,945,050; and U.S. Pat. No. 5,015,580.

The herein-described tobacco matrix from cultured tobacco cells grown in vitro provides various advantages. The tobacco matrix, particularly when grown without added light, is substantially devoid of dark pigment that occurs in conventionally-grown tobacco plants, especially tobacco that has been harvested and cured. This makes the cultured tobacco especially desirable for smokeless tobacco products, where the lack of pigment can be easily observed.

Additionally, the cultured tobacco material exhibits a neutral flavor profile, with little or none of the harsh, astringent, and/or bitter flavors normally found in conventionally-grown tobacco. This feature is especially advantageous in view of the possibility that culture conditions may be manipulated to achieve tobacco products that may enhance the sensorial experience (e.g., flavor) of utilizing the products. The neutral flavor profile may make added flavors (whether added in culture or at a later stage) more readily detectable by consumers.

Furthermore, a tobacco matrix as described herein may have a reduced level of undesired biological activity as compared to conventionally-grown tobacco: for example, reduced cytotoxicity and/or reduced mutagenicity. Cultured tobacco cells grown in a controlled environment are expected to have reduced levels of tobacco-specific nitrosamines (TSNAs) and reduced levels of heavy metals such as cadmium.

The cells grown in culture are capable of producing a range of metabolites observed in traditionally grown leaves (e.g., flavors, enzymes, amino acids, etc.), and can exhibit additional properties useful for the improvement of tobacco products and/or development of alternative tobacco products.

B. Products Incorporating Cultured Tobacco Material

Various embodiments are directed to consumable products incorporating a tobacco matrix grown from culture. Such products, for example smoking articles and smokeless products, optionally include conventionally-grown tobacco in addition to the tobacco matrix. Tobacco products include lit-end (i.e., smokeable) and smokeless products. Lit-end products include cigarettes, cigars, and the like, as well as loose tobacco intended for smoking (for example in a pipe or hand-rolled cigarette).

Smokeless tobacco products incorporating a tobacco matrix as disclosed herein may be in any format suitable for comfort in a consumer's oral cavity. Smokeless tobacco products contain tobacco in any form, such as moist smokeless tobacco (MST), chewing tobacco, or orally-usable pouched smokeless tobacco products. The tobacco itself may take the form of dried particles, shreds, granules, powders, or a slurry (i.e., tobacco extract), deposited on, mixed in, surrounded by, or otherwise combined with other ingredients in any format, such as flakes, films, tabs, foams, or beads. Smokeless tobacco products may be wrapped with a material, which may be edible (i.e., orally disintegrable) or non-edible. Liquid contents of smokeless tobacco products can be enclosed in a form, such as beads, to preclude interaction with a water-soluble wrapper. The wrapper may be shaped as a pouch to partially or completely enclose tobacco-incorporating compositions, and/or to function as an adhesive to hold together a plurality of tabs, beads, or flakes of tobacco, thereby forming a pouched tobacco product. A wrapper may also enclose a moldable tobacco composition that conforms to the shape of a consumer's mouth. An orally disintegrable wrapper may enclose smokeless tobacco and may be formed on continuous thermoforming or horizontal form/fill/seal equipment or other suitable packaging equipment using edible films (which may or may not contain tobacco). Exemplary materials for constructing a wrapper include film compositions comprising hydroxypropyl methylcellulose ("HPMC"), carboxymethylcellulose ("CMC"), pectin, alginates, pullulan, and other commercially viable, edible film-forming polymers. Other wrapping materials may include pre-formed capsules produced from gelatin, HPMC, starch/carrageenan, or other commercially available materials. Such wrapping materials may include tobacco as an ingredient. Wrappers that are not orally disintegrable may be composed of woven or nonwoven fabrics, of coated or uncoated paper, or of perforated or otherwise porous plastic films. Wrappers may incorporate flavoring and/or coloring agents. Smokeless products can be assembled together with a wrapper utilizing any method known to persons skilled in the art of commercial packaging, including methods such as blister packing and stick-packing, in which a small package can be formed by a vertical form/fill/seal packaging machine.

It may also be advantageous to add one or more additional components or other additives to a tobacco product as described herein. These components may include, but are not limited to, the following: flavorants, colorants, sweeteners, such as xylitol, bulking agents, fillers, anti-adherent compounds, dispersing agents, moisture absorbing compounds, binder, chemesthetic agents, such as warming agents or cooling agents, and film-forming agents. Such components may be included in any or all portions of the product, for example in a tobacco filler and/or a wrapper. Such components may be used in amounts sufficient to achieve their intended effects.

Products including a tobacco matrix as described herein may also include a blend of conventionally-grown tobacco, non-tobacco smoking material, tobacco extender, tobacco dust, and/or reconstituted tobacco.

EXAMPLES

Example 1

Initiation of Tobacco Callus Cultures from Explants

Preparation of Growth Media: Tobacco cultures can be stably established and propagated indefinitely in many types of media, including Murashige and Skoog (MS), a medium commonly utilized for providing nutrients to various plant-tissue cultures. MS is regarded as a 'high salt' medium, and can be obtained from various commercial sources as a powder or a liquid concentrate. Growth regulators can be purchased similarly from various commercial vendors. Methods for accurate and reproducible preparation of growth medium are known to persons skilled in the art. Reagents obtainable from reliable vendors include: Callus Media agar plates (100×20 mm) from Teknova No:2M9280; Murashige and Skoog Basal Media with 2% Sucrose from Teknova No:(1L); 2,4-D (2,4-Dichlorophenoxyacetic Acid from Sigma, Cat. No: D-6679 (25g); IAA (Indole-3-acetic acid, from Sigma, Cat. No: 12886. MS Basal Liquid Medium with 2% Sucrose+1.5 μg/ml IAA can be prepared by combining 1.0 ml of a 1.5 mg/ml IAA solution into 1L of MS Basal Media with 2% sucrose, under aseptic conditions. The media should be mixed well, and allowed to equilibrate for approximately 10-15 minutes prior to contact with cells. Toshio Murashige and Folke Skoog, "A Revised Medium for Rapid Growth and Bio Assays with Tobacco Tissue Cultures," Physiologia Plantarum, Vol. 15., pp. 473-497 (1962), which is incorporated herein by reference in its entirety.

Initiation of Explants: Under aseptic conditions, the terminal (e.g., 12 inches) portion of the main stem of a tobacco plant can be severed, removing all leaves and side buds. The stem can be further divided into 4 smaller pieces and placed in a beaker containing 70% ethanol (made with sterile water) for 3 minutes. The stem pieces are placed in sterile water three times, using sterile 1 L beakers for washes. A cylinder of pith can be removed and placed into a sterile Petri dish using a sterile cork borer. About ¼ of an inch can be removed from each side of the cylinder of the pith. Using a sterile scalpel and forceps, the pith can be further sliced into thin discs, approximately 1-2 mm thick. The discs can be placed, cut-side down, onto MS agar plates supplemented with 2,4 D. Parafilm® can be wrapped around the lid of plates, and the plates incubated at 27° C. in the dark for approximately 1 month.

Sub-culturing of Callus Tissue: Sharp forceps or a sterile scalpel can be used to divide callus tissue. Approximately 2 weeks after the explants have formed a substantial callus, each piece can be divided into two or three pieces no less than 10 mm×10 mm. The pith can be removed at this point. Using sterile forceps, the friable callus can be removed from around the pith, and placed onto a new MS agar plate. This can be repeated until all calluses from the old plate have been transferred to new plates. Parafilm® can be wrapped around the lids of new plates and the plates incubated in the dark at 27° C.

Example 2

Initiation of Tobacco Cell Suspension Cultures from Callus Tissue

Initiation of Suspension Cultures: The developing callus can be transferred to a 1 L sterile baffle bottom flask filled with 500 ml MS liquid media using sterilized forceps. Sufficient callus tissue can be transferred in small pieces to initiate a good suspension culture (i.e., covering the top of liquid media). The flask can be capped lightly, and placed in a dark shaking incubator set at 110-112 rpm at 27° C.

Sub-culturing of Suspension Cultures: The suspension can be transferred to new media, every 7-10 days, when the suspension culture becomes very opaque. A new flask containing 300ml of MS liquid media with 150 ml of the growing culture can be initiated by adding the liquid media to the suspension culture in a 2-to-1 ratio. The growing suspension culture to be transferred should be measured, for example, utilizing a 100 ml disposable graduated cylinder. The resulting culture should have a yellow, slightly thick appearance. To avoid anoxic or dying cells, the suspension cultures should not be resting without shaking for more than 30 min. MS liquid media can be added to original cultures for easier inoculation of new flasks, if necessary.

Example 3

Harvesting Tobacco Cells from Suspension Cultures

After at least 3 passages in liquid media, the flask containing tobacco cells can be harvested by various methods, including filtration, which can be extremely efficient. The entire content of the flask can be poured through a filter unit (medium Buchner funnel with nylon mesh filter material) while applying a vacuum. The sample is washed in the filter unit by adding 100 ml of tap water, and the remaining liquid can be removed with the vacuum. This wash can be followed by two washes with 100 ml of MilliQ® water. After the final wash, the sample can be allowed to air dry as much as possible. Subsequently, samples can be freeze-dried, or can be subjected to equivalent procedures. Preferably, the resulting material is stored under dry conditions to prevent uptake of moisture.

Although the invention has been described with reference to particular embodiments and examples, it should be understood that various modifications can be made without departing from the spirit of the invention. The various parts of the disclosure including the abstract, summary, and the title are not to be construed as limiting the scope of the present invention, as their purpose is to enable the appropriate authorities, as well as the general public, to quickly determine the general nature of the invention. Unless the term "means" is expressly used, none of the features or elements recited herein should be construed as means-plus-function limitations pursuant to 35 U.S.C. § 112, ¶6. Accordingly, the invention is limited only by the claims.

What is claimed is:

1. A consumable product comprising a matrix of cultured tobacco cells grown in vitro, wherein the matrix of cultured tobacco cells comprises at least 5% by weight extracellular matrix and the product is a smokeless tobacco product or a lit-end tobacco product.

2. The product of claim 1, wherein the matrix of cultured tobacco cells has substantially reduced harsh, astringent, and/or bitter flavors as compared to conventionally-grown tobacco.

3. The product of claim 1, wherein the cultured tobacco matrix is derived from a culture of genetically-modified tobacco.

4. A consumable product comprising a matrix of cultured tobacco cells grown in vitro, wherein the matrix of cultured tobacco cells comprises at least 5% by weight extracellular matrix wherein the product comprises a blend of said matrix and one or more components selected from the group consisting of conventionally-grown tobacco, non-tobacco smoking material, tobacco extender, tobacco dust, and reconstituted tobacco.

5. A consumable product comprising a matrix of cultured tobacco cells grown in vitro, wherein the matrix of cultured tobacco cells comprises at least 5% by weight extracellular matrix wherein the product further comprises one or more components selected from the group consisting of flavorants, colorants, sweeteners, bulking agents, fillers, anti-adherent compounds, dispersing agents, moisture absorbing compounds, binder, chemesthetic agents, and film-forming agents.

6. The product of claim 5, wherein the product is an orally-usable pouched smokeless tobacco product.

* * * * *